United States Patent [19]

Jacobson et al.

[11] Patent Number: 4,968,601

[45] Date of Patent: Nov. 6, 1990

[54] METHOD FOR DIAGNOSING LATENT VIRAL INFECTION

[75] Inventors: Steven Jacobson, Kensington; Dale E. McFarlin, Potomac, both of Md.

[73] Assignee: The United States of America as represented by the Dept. of Health & Human Services, Washington, D.C.

[21] Appl. No.: 153,933

[22] Filed: Feb. 9, 1988

[51] Int. Cl.$^5$ ............................................. C12Q 1/70
[52] U.S. Cl. ...................................... 435/5; 435/235; 435/239
[58] Field of Search ........................... 435/235, 239, 5

[56] References Cited

PUBLICATIONS

Belline, et al., *J. Neuroimmunol.*, 11:149–161, 1986.
Sodroski, et al., Science, 225:381–385, 1984.
Ohta, et al., *J. Immunol.*, 137:3440–3442, 1986.
Hauser, et al., *Nature*, 322:176–177, 1986.
Ho, et al., *N. Eng. J. Med.* 313:1493–1497.

*Primary Examiner*—Sam Rosen
*Attorney, Agent, or Firm*—Mishrilal Jain

[57] ABSTRACT

A method for diagnosing latent viral infection is described. The method utilizes an agent such as OKT3 to stimulate CD3 receptor complex on T-cell line so that the latent virus harbored in the T cells is expressed and then the virus is identified by standard techniques.

13 Claims, 4 Drawing Sheets

METHOD FOR DIAGNOSING LATENT VIRAL INFECTION

BACKGROUND OF THE INVENTION

1. Technical Field

The present invention is related generally to the isolation and identification of new viruses. More particularly, the present invention is related to a novel technique for expression of latent viruses and then isolation and identification of the same. Using this technique, a new virus related to HTLV 1 family of retroviruses has been isolated and characterized.

2. State of the Art

A problem in identifying the causative factor in certain diseases or pathological conditions, particularly when suspected of viral origin, is the detection of the virus itself as a concomitant of the disease. The virus may simply infect the cells and remain dormant. Detection of such latent viruses becomes difficult for the lack of enough viral population which can be monitored by the currently available techniques.

SUMMARY OF INVENTION

It is, therefore, an object of the present invention to provide a method for isolating and identifying new viruses.

It is a further object of the present invention to provide a novel technique for isolation of a new human T cell leukemia retrovirus from lymphocytes in the blood and cerebrospinal fluid from patients with neurological diseases or other human disorders related to retroviruses.

Other objects and advantages of the present invention will become evident from the following detailed description of the invention.

BRIEF DESCRIPTION OF DRAWINGS

These and other objects, features and many of the attendant advantages of the invention will be better understood upon a reading of the following detailed description when considered in connection with the accompanying drawings wherein.

DETAILED DESCRIPTION OF INVENTION

Figure 1A:
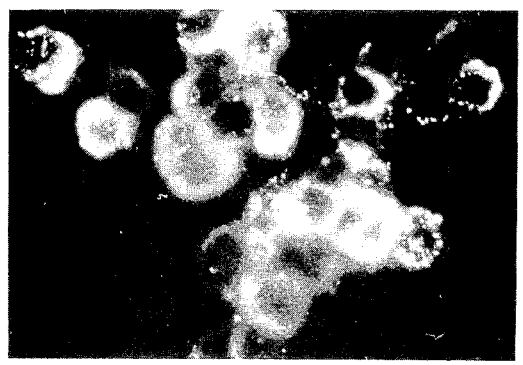
FIG. 1 shows: (A) T cell lines derived from PBL of patient I stained with the HTLV-I specific p19 antibody; (b) T cell lines derived from CSF of patient II stained with the HTLV-I specific p19 antibody. Similar staining was obtained with the anti-p24 antibody, (c) Fluorescence with the anti-p19 antibody of cells derived from the co-cultivation of normal PBL with the irradiated (10000R) T cell line of the PBL of patient I. Similar staining was obtained with the anti-p24 antibody. Co-cultured cells were maintained as described in the text except 0.3% phytohemagglutinin (GIBCO, Grand Island, N.Y.) was added to the media.

The advantages of the present invention are achieved by a method of isolating latent virus from human T cells, comprising the steps of (a) establishing in a defined culture medium a human T cell line from a patient suspected of carrying viral infection; (b) inducing CD3 receptor complex on said T cell line using an agent which activates the CD3 receptor complex, to express latent virus harbored in said T cells; (c) then isolating and characterizing the virus expressed by said T cell by conventional techniques.

As an example, a new virus related to HTLV-1 family of retroviruses has been isolated using the method of the present invention. The virus has been preserved in a human T cell line as a biologically pure culture which replicates only the new virus without contamination of any kind, when said T cell line is grown under suitable conditions.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned hereunder are incorporated herein by reference.

Tropical spastic paraparesis (TSP), a slowly progressive myelopathy associated with increased serum and cerebrospinal fluid (CSF) antibodies to the human T-lymphotropic retrovirus type I (HTLV-1) has been observed in many regions. A similar condition termed HTLV-1 associated myelopathy (HAM) occurs in the Kagoshima prefectures of Japan. Some reports also suggest an involvement of an HTLV-I related virus in multiple sclerosis (MS). Magnetic resonance imaging (MRI) and electrophysiological studies indicate that, similar to MS, TSP lesions are disseminated throughout the nervous system. Complete virus has been consistently difficult to isolate from patients with TSP using techniques that have been successful in individuals with adult T cell leukemia (ATL) associated with HTLV-1. But, the present invention, for the first time presents a method for the isolation of an HTLV-1 like virus from T cell lines derived from the peripheral blood and CSF of TSP patients. The monoclonal antibody OKT3 was used to generate non-transformed T cell lines that express HTLV-1 antigens. Infectivity of the virus was demonstrated by co-cultivation and complete, replicating virions were visualized ultrastructurally.

It is noted that although OKT3 is employed as a preferred agent, any agent which activates CD3 receptor complex to express latent virus in a T cell line could be used.

ESTABLISHING T CELL LINES:

T cell lines were derived from Peripheral blood lymphocytes by culturing $1.2 \times 10^7$ cells in 10 mls of RPMI (GIBCO, Grand Island, N.Y.) containing 5% human AB serum plus 10% interleukin 2 (Cellular Products, Buffalo, N.Y.) and a 1:5000 dilution of ascites of the murine monoclonal antibody OKT3 (ATCC catalog No. CRL8001). Cells were passaged at a density of $5-10 \times 10^5$/ml, $5 \times 10^5$ cells were subcultured, and irradiated (6000R). Allogeneic feeders were added at a 5–7 fold excess. CSF T cell lines were derived by culturing $0.5-1.0 \times 10^5$ CSF lymphocytes in the above medium plus irradiated autologous or allogeneic feeders. Indirect immunofluorescence assays were done on acetone fixed cytospin preparations. Cells were incubated for 30 minutes with the murine monoclonal antibodies specific for HTLV-1 p19 or p24 gag protein (Biotech, Research, Rockville, Md., catalog no. 7050,7051). Slides were washed in phosphate buffered saline (PBS-, GIBCO, Grand Island, N.Y.) and then stained for 30 minutes with an F(ab')2 sheep anti-mouse IgG conjugated to FITC (Cappel, Cochranville, Pa.). Cells were washed in PBS- containing a 1:2000 dilution of a 1% Evans Blue solution which under ultraviolet illumination fluoresces red to contrast the antibody-specific yellow-green FITC staining.

ANALYSIS OF IMMUNE COMPLEX

The T cell line ($1 \times 10^7$ cells) derived from PBL of the TSP patient I cultured for one passage in the absence of OKT3 was labeled with 0.75 mci of $^{35}$S-methionin (Amersham, Chicago, Ill.) in 20 ml of methionine-free RPMI supplemented with 5% of the normal amount of methionine for 18 hours. After centrifugation and washing with PBS-, the cells were lysed and immunoprecipitation was performed by a modification of the method of Bellini, et al., *J. Neuroimmunol.* 11,149–161 (1986). Aliquots of lysate containing $3 \times 10^6$ dpm were cleared with 100 μl of 10% *S. aureus* Cowan I (Sigma, St. Louis, Mo.) in 300 μl of radioimmunoprecipitation assay buffer (RIPA) containing 0.5% myoglobin (Sodroski, et al., (1984) *Science* 225,381–385). The supernatant was incubated for 1 hour at 4° C. with *S. aureus* which had been (A) coated first with the IgG fraction of a rabbit anti-mouse IgG (Cappel, Cochranville, Pa.) and then for 1 hour with 10 μl of mouse ascites, or (B) coated directly with the human serum to be tested. The *S. aureus* was washed and the immune complex dissociated and analyzed by SDS-PAGE electrophoresis.

DNA ANALYSIS

Hut-102 or the PBL T cell line of patient I was homogenized in 4M Guanidine SCN and the homogenate was layered over a cushion of 5.7M CsCl. After centrifugation at 30,000 rpm for 18 hours the DNA above the cushion was collected, dialyzed in 10 mM Tris HCL pH 7.4, 1 mM Na$_4$EDTA and digested with proteinase K (200 gm/ml). After extraction with phenol CHCl$_3$ and dialysis, 10 g of each DNA was digested with restriction endonucleases, the products were separated by electrophoresis through a 0.6% agarose gel and transferred to a biotrans membrane filter for hybridization to a full length HTLV-1 probe radiolabelled with $^{32}$P (50% formamide, 0.75M NaCl, 43° C., 60 hours). After washing successively in $2 \times$ SSC, $0.1 \times$ SC in 0.1% SDS at ambient temperature, (about 22° C. to 25° C.) and $0.1 \times$ SSC in 0.1% SCS at 43° C., the filters were dried and exposed overnight at $-100°$ C. to X-ray film in a cassette with two intensifying screens.

ULTRASTRUCTURE ANALYSIS

The T cell line derived from patient I was used for ultrastructural analysis. A suspension culture containing approximately $5 \times 10^6$ cells was pelleted at $500 \times g$ at 4° C., fixed by 2.5% glutaraldehyde in phosphate buffer (pH 7.3) for 60 minutes and post-fixed by 1% osmium tetroxide for 60 minutes. The pellets were then passed through a graded series of ethyl alcohol, cleared in propylene oxide and embedded in Epon 812. Thin sections for electron microscopy (EM) were stained with uranium and lead salts.

Figure 1B:
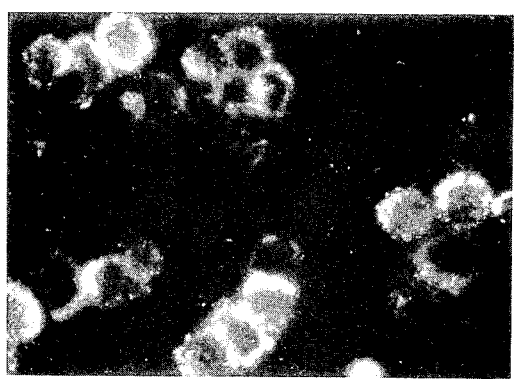

In accordance with the methods described above, T cell lines were established from two HTLV-1 seronegative controls and seven TSP patients (Table 1). Purified peripheral blood lymphocytes (PBL) or CSF cells were cultured in the presence of interleukin-2 (IL-2), irradiated allogeneic feeder cells, the monoclonal antibody OKT3, and passed every 5–7 days. OKT3 was used as a non-selective activator of T cells since it stimulates the antigen-specific T cell receptor-CD3 complex. Fixed cytocentrifuge preparations of the T cell lines were assessed by indirect immunofluorescence with monoclonal antibodies specific for HTLV-1 p19 and p24 gag proteins. Twelve T cell lines derived from the PBL and CSF of six of the seven TSP patients contained large amounts of viral antigen detected by immunofluorescence (FIG. 1 A, B). The expression of HTLV-1 related antigens in the TSP cell lines varied with passage history (Table 1). T cell lines derived for PBL of controls and from patient III did not react with these antibodies. Viral antigen was not detected in either fresh PBL or cultured, unstimulated PBL from the TSP patients.

Figure 2A:
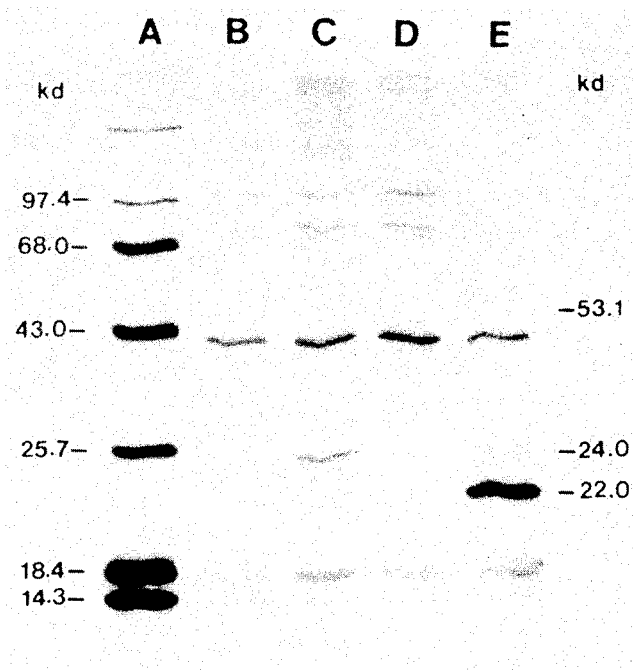
FIG. 2 shows: Lane A—molecular weight standards: Lane B—immunoprecipitate with an irrelevant control mouse ascites: Lane C—Immunoprecipitate with the murine monoclonal anti-p24 (Biotech Research, Rockville, Md.); Lane D—immunoprecipitate with an HTLV-1 seronegative normal control serum; Lane E—immunoprecipitate with the serum of the TSP patient 1.
FIG. 2B shows: Lane 1, Hut-102 DNA digested with Pst 1; Lane 2, TSP T cell line DNA digested with PST 1; Lane 3; TSP T cell line DNA with EcoR1.

T cell lines from patient I were thoroughly studied and HTLV-1 related gag proteins confirmed by immunoprecipitation. Control sera reacted with a number of cellular proteins (FIG. 2A lanes B and D). However, the TSP sera and the monoclonal antibody anti-P24 specifically immunoprecipitated three proteins with approximate molecular weights of 53 kd, 24 kd and 22 kd (FIG. 2A lane C and E). By Western blot, the anti-p24 antibody reacted with similar HTLV-1 proteins which are believed to represent processed intermediates of the gag protein. Similar patterns were observed using radiolabelled transformed cell lines infected with conventional HTLV-1 (Hut 102). Serum from an ATL patient immunoprecipitated the 24 kd and 22 kd peptides, but no reactivity with the 53 kd protein was observed.

Figure 2B:
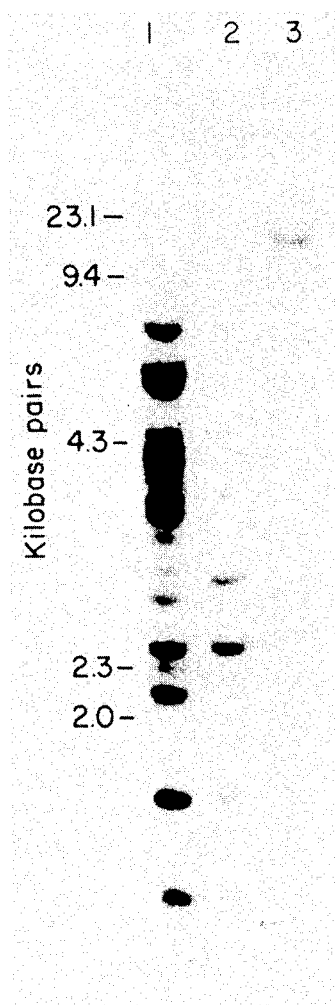

DNA from the PBL T cell line from patient I was hybridized with a 9 kb HTLV-1 probe as described by Shaw, et al., (1984), PNAS (USA); 81,4544–4582. Bands corresponding to molecular weights of 2.4 kb, 1.6 kb, and 1.3 kb, were observed in the PST 1 digest (FIG. 2B, lane 2). Identical bands were observed when the control Hut-102 cell line, known to contain multiple proviral copies and integration sites, was probed (FIG. 2B, Lane 1). These are consistent with the restriction map of HTLV-1. An Eco R1 digest of the TSP T cell line DNA (FIG. 2B, lane 3) produced one band which could represent either monoclonal integration or integration of multiple proviruses plus flanking sequences. The 2.9 Kb Pst 1 band (FIG. 2B, lane 2) is consistent with an interpretation of monoclonal integration.

Figure 1C:

To determine if infectious virus was present, PBL from an HLA mis-matched normal individual were-co-cultured with irradiated (10,000R) PBL T cell line of TSP patient I. The co-cultured cells had the HLA phenotype of the recipient PBL and after the first passage, 40% of cells contained HTLV-1 related proteins (FIG. 1C). Recipient cells cultured in the absence of the TSP T cell line did not react with the anti-HTLV-1 antibodies. The irradiated TSP T cell line did not grow when cultured alone.

Figure 3A:
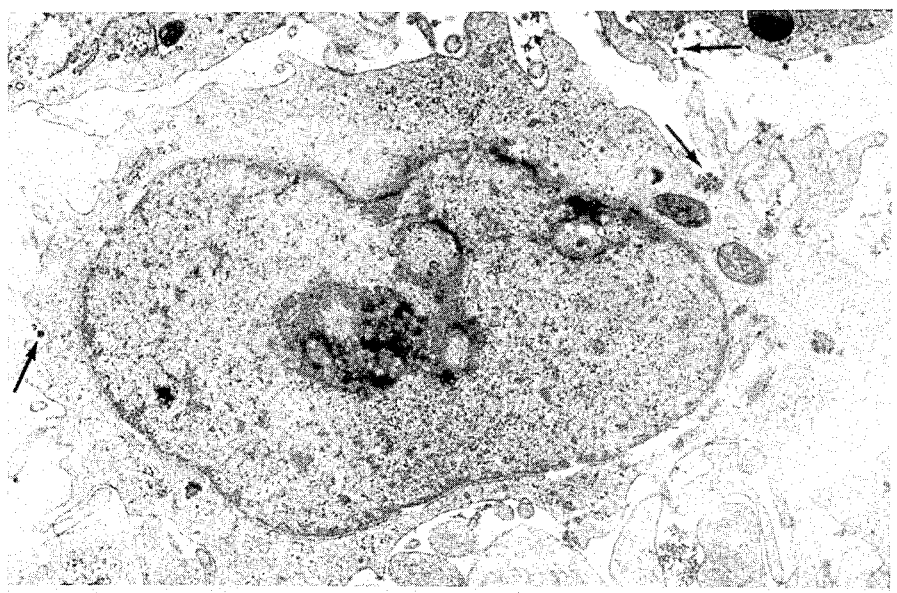
FIG. 3 (A) is a low power electron micrograph illustrating that the majority of cells are small (10 nm in diameter) densely staining PBL. The homogeneous, granular cytoplasm, mitochondria and scattered rough endoplasmic reticulum are noteworthy. The dense particles (arrows) in the extracellular space are virions. $\times 8,750$. (B) A small group of virions is seen among smaller tubular profiles which suggest dissociated capsid material. One virion (arrow) contains a capsid which is doughnut-shaped. Spike material is occasionally seen (upper right) around the envelope. $\times 100,000$. (C) A small group of virions is seen along a cell surface. Note that each possesses a core (nucleoid or capsid) which sometimes has an icosahedral profile, a doughnut shape, or a honeycomb appearance, plus a distinct envelope. $\times 75,000$. (D) A group of virions is seen at the surface of a cell from the HTLV-1 infected cell line, C1-MJ. Note that the virions appear identical to those in FIG. 3C. $\times 75,000$. (E-G) Stages in viral budding: (E) the accumulation of viral nucleoid beneath a membrane protrusion, $\times 110,000$; (F) the outpouching of the viral bud which now contains a horse-shoe shaped nucleoid, $\times 120,000$; (G) a near completely budded virion containing a mature nucleoid, $\times 140,000$.
Figure 3B:
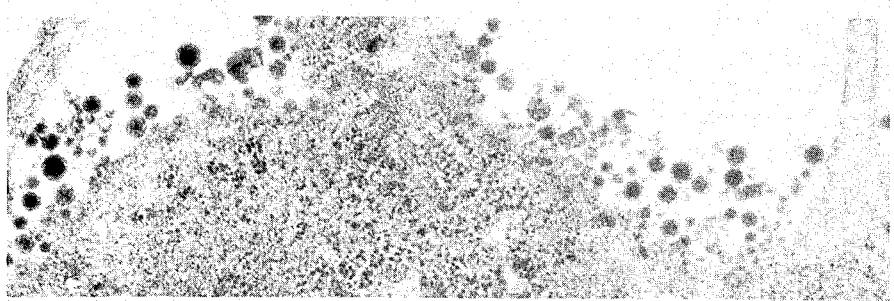
Figures 3C, 3D, 3E:
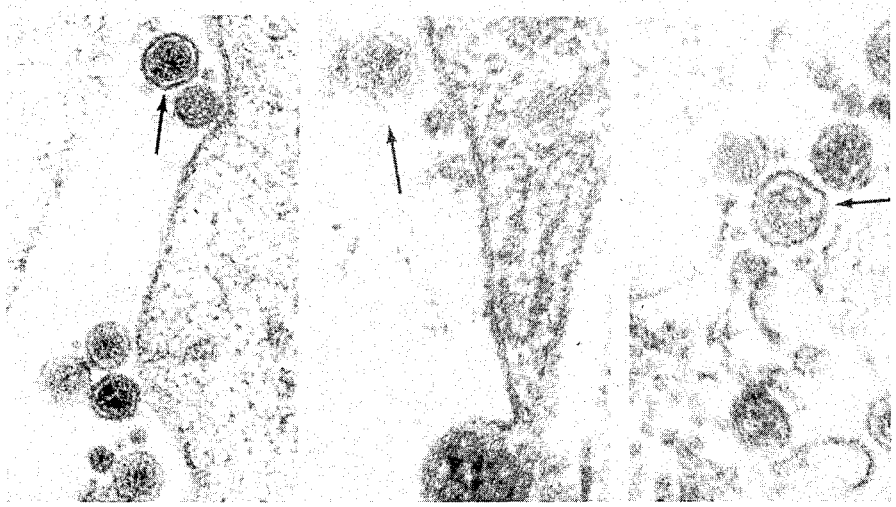

T cell lines from patient I, II and IV were used for ultrastructural studies (FIG. 3). Complete and intact viral particles were observed extracellularly in all these lines. Most often, virions were cell-free (FIG. 3 A-C), but immature virions budding from the plasmalemma were common (FIG. 3 E-G). Mature virions ranged in diameter from 80-120 nm (FIG. 3B, C) and consisted of nucleocapsid surrounded by an envelope. The virions were indistinguishable from those in the HTLB-1 carrier cell line, C1-MJ (FIG. 3D). In some sections, the icosahedral nature of the capsid was evident, giving an hexagonal profile with a honeycomb-like substructure. Viral replication involved the assembly of capsid material beneath the plasmalemma followed by budding (FIG. 3 E-G). Smaller circular or tubular profiles in the extracelular space were intermixed among virus particles (FIG. 3 B, C).

The association of TSP with HTLV-1 is based mainly on serological findings. Demonstration of an HTLV-1 related virus from both PBL and CSF of six TSP patients in this virus in the pathogenesis of this disorder. Infection by HTLV-1 may lead to immunopathological or autoimmune abnormalities which cause the neurological disease. Elucidation of the underlying pathogenetic mechanisms could have broader implication because an association between HTLV-1 and MS has been proposed (Ohta, et al., (1986) J. Immunol.; 137,3440-3443 and Hauser, et al., (1986) Nature; 322,176-177). Neurological abnormalities in TSP are not confined to the spinal cord and similar to classical MS, involve other sites. Although three of six TSP patients in whom an HTLV-1 like virus was demonstrated had MRI lesions consistent with disseminated involvement, the neuropathological basis for these lesions is not fully established.

Virus was not demonstrated in the T cell lines derived from patient III (Table 1) who was the spouse of patient II and was probably exposed to the same agent. However, peripheral blood DNA from patient III demonstrated strong hybridizing bands with the HTLV-1 9 kb probe. It is not known why viral antigen was not detected in this patient's lymphocytes but there is precedent for such a phenomenon. For example, HIV-1 cannot be isolated from all patients with neurologic syndromes associated with AIDS (Ho, et al., (1985) N. Eng. J. Med.; 313,1493-1497).

A distinct property of conventional HTLV-1 is the capacity to immortalize and transform normal lymphocytes. In contrast, the T cell lines derived from the six TSP patients have remained IL-2 dependent. Additional biological differences between the virus associated with TS and conventional HTLV-1 have been identified. Infection of a CD4+ HLA class II restricted cytotoxic T cell line specific for influenza virus by co-cultivation with the Hut 102 cell line inhibited the cytotoxic function. No inhibition was observed when the influenza T cell line was comparably infected by the PBL T cell line of TSP patient I.

A deposit of the new virus cultured in a T cell line from a normal individual known to be free from retrovirus infection (00134TSP)has been made at the ATCC, Rockville, Md. on Feb. 4, 1988 under the accession number CRL 9640. The deposit shall be viably maintained, replacing if it became non-viable, for a period of 30 years from the date of the deposit, or for 5 years from the last date of request for a sample of the deposit, whichever is longer, and made available to the public without restriction in accordance with the provisions of the law. The Commissioner of Patents and Trademarks, upon request, shall have access to the deposit.

In summary, demonstration of an HTLV-1 related virus in 12 TSP cell lines was accomplished by T cell activation with the monoclonal antibody OKT3. Some T cell lines required the presence of OKT3 in addition to IL-2 for growth. Stimulation of the T cell receptor complex may enhance the endogenous production of viral proteins similar to activation pathways described for HTLV-1 and HIV-1. Collectively, the data indicate that viruses isolated from TSP patients are related to HTLV-1 but may represent variants of HTLV-1 or possibly new members of the human retrovirus family which lack transforming or lytic properties. This would be consistent with the absence of malignancies or lymphoproliferative abnormalities in patients with TSP.

The biologically pure culture of the new virus of the present invention can, of course, be utilized in a pharmaceutical composition either alive or killed, attenuated or virulent, in whole or in part, for the preparation of a vaccine following standard techniques well known to one of ordinary skill in the art.

TABLE 1

Detection of HTLV-I Associated Gene Products in T Cell Lines Derived from Peripheral and Cerebrospinal Fluid

| TSP Patient | Nationality | Earliest Passage When Cultures* HTLV-I P19 Positive | | Percent Positive HTLV-1 P19 Antigen at Current Passage # | |
|---|---|---|---|---|---|
| | | PBL | CSF | PBL | CSF |
| I | Haitian | P8 | P7 | 75% (P29) | 60% (P7) |
| II | Columbian | P11 | P9 | 70% (P25) | 50% (P23) |
| III | Columbian | — | — | 0% (P10) | 0% (P10) |
| IV | Columbian | P5 | P4 | 15% (P5) | 75% (P11) |
| V | Columbian | P5 | P3 | 30% (P11) | 15% (P10) |
| VI | Columbian | P3 | P2 | 25% (P11) | 50% (P9) |
| VII | Jamaican | P1 | P3 | 30% (P7) | 75% (P4) |

*Ten percent positivity as determined by indirect immunoflurorescence with the anti-HTLV-1 P19 antibody.

It is understood that the examples and embodiments described herein are for illustrative purposes only and that various modifications or changes in light thereof will be suggested to persons skilled in the art and are to be included within the spirit and purview of this application and scope of the appended claims.

What is claimed is:

1. A process for diagnosing latent viral infection, comprising the steps of:
   (a) establishing in a culture medium a human T cell line from a patient suspected of harboring latent viral infection;
   (b) expressing latent virus harbored in the T cell line of step (a) by stimulating said T cell line by an agent which stimulates CD3 complex on said T cell line; then
   (c) identifying the virus expressed in step (b) by any standard technique.

2. The process of claim 1 wherein the agent used to activate the CD3 receptor complex is OKT3.

3. The process of claim 1 wherein interleukin-2 is used to stimulate growth of the T cell line.

4. The process of diagnosing latent viral infection according to claim 1 wherein viral DNA is identified by means of a probe using hybridization techniques.

5. The process of claim 4 wherein the probe is radiolabelled.

6. The process of claim 1 identifying the virus or viral particles.

7. The process of diagnosing latent viral infection according to claim 1 by identifying viral antigens.

8. The process of claim 7 wherein the viral antigen is identified using a Western blot test.

9. The process of claim 7 wherein the viral antigen is identified using a competitive immunoassay.

10. The process of claim 9 wherein the assay is an indirect immunofluorescence test.

11. A process of claim 7 wherein the viral antigen is identified using an immunofluroescence techniques.

12. The method of claim 6 identifying the virus or viral-particles by electron microscopy.

13. A method for isolating and identifying a virus from a patient harboring latent viral infection, comprising the steps
   (a) culturing T cells from peripheral blood lymphocytes obtained from a patient suspected of harboring latent viral infection, in a defined culture medium in the presence of an activator that stimulates said T cells so that latent virus is expressed;
   (b) then isolating and characterizing the expressed virus by conventional techniques.

* * * * *